US009252870B2

(12) United States Patent
Mears et al.

(10) Patent No.: US 9,252,870 B2
(45) Date of Patent: Feb. 2, 2016

(54) HANDHELD DIABETES MANAGER WITH A USER INTERFACE FOR DISPLAYING A STATUS OF AN EXTERNAL MEDICAL DEVICE

(71) Applicant: Roche Diabetes Care, Inc., Indianapolis, IN (US)

(72) Inventors: Mark G. Mears, Westfield, IN (US);
Mark Nierzwick, Brownsburg, IN (US);
Phillip E. Pash, Indianapolis, IN (US);
Vincent R. Rizzo, Indianapolis, IN (US);
Bettina Steiner, Kaiserstuhl (CH);
Kristin M. Westerfield, Indianapolis, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 29 days.

(21) Appl. No.: 13/661,082

(22) Filed: Oct. 26, 2012

(65) Prior Publication Data

US 2013/0172708 A1   Jul. 4, 2013

Related U.S. Application Data

(60) Provisional application No. 61/581,149, filed on Dec. 29, 2011.

(51) Int. Cl.
*A61B 5/145* (2006.01)
*H04B 7/26* (2006.01)
(Continued)

(52) U.S. Cl.
CPC ............... *H04B 7/26* (2013.01); *A61B 5/0002* (2013.01); *A61B 5/14532* (2013.01); *A61B 5/7435* (2013.01); *A61M 5/14244* (2013.01); *A61M 5/1723* (2013.01); *G06F 19/3406* (2013.01); *G06F 19/3468* (2013.01);
(Continued)

(58) Field of Classification Search
CPC ............ G06F 19/3468; G06F 19/3406; A61B 5/7435; A61B 5/0002; A61B 5/14532; H04W 84/20; H04W 4/001; A61M 5/1723; A61M 2205/35; A61M 2205/3569; A61M 2205/3584; A61M 5/14244
USPC ................... 700/17, 18, 83, 266; 340/539.12; 702/19, 22, 23, 25, 31, 32; 600/365
See application file for complete search history.

(56) References Cited

U.S. PATENT DOCUMENTS 7,291,107 B2 * 11/2007 Hellwig .............. G06F 19/3468
                                                        600/300
7,912,655 B2    3/2011 Power et al.
(Continued)

*Primary Examiner* — Shogo Sasaki
(74) *Attorney, Agent, or Firm* — Harness, Dickey

(57) ABSTRACT

A handheld diabetes manager has a graphical user interface for displaying status of an external medical device and includes a port configured to receive a test strip and a blood glucose measurement module. The diabetes manager includes a communications module that selectively communicates via a wireless data link with an external medical device to receive status data pertaining to the operation of the external medical device, and a user interface module in data communication with the blood glucose measurement module and the communications module. The graphical user interface includes a status screen that presents data pertaining to a glucose measure determined by the blood glucose measurement module concurrently with the status data received from the external medical device, such that the status data of the external medical device is presented on the status screen only when the communication module is in data communication with the external medical device.

8 Claims, 11 Drawing Sheets

(51) Int. Cl.
*A61B 5/00* (2006.01)
*A61M 5/142* (2006.01)
*A61M 5/172* (2006.01)
*G06F 19/00* (2011.01)
*H04W 4/00* (2009.01)
*H04W 84/20* (2009.01)

(52) U.S. Cl.
CPC .......... *H04W 4/001* (2013.01); *A61M 2205/35* (2013.01); *A61M 2205/3569* (2013.01); *A61M 2205/3584* (2013.01); *H04W 84/20* (2013.01)

(56) References Cited

U.S. PATENT DOCUMENTS

| | | | |
|---|---|---|---|
| 7,976,467 B2 | 7/2011 | Young et al. | |
| 2008/0234992 A1* | 9/2008 | Ray | G06F 19/345 703/2 |
| 2008/0287922 A1* | 11/2008 | Panduro | G06F 19/3456 604/890.1 |
| 2008/0312512 A1* | 12/2008 | Brukalo | A61B 5/0002 600/300 |
| 2008/0312584 A1* | 12/2008 | Montgomery | A61M 5/14244 604/67 |
| 2008/0312585 A1 | 12/2008 | Brukalo et al. | |
| 2009/0018495 A1* | 1/2009 | Panduro | G06F 19/3468 604/67 |
| 2009/0113295 A1 | 4/2009 | Halpern et al. | |
| 2009/0305317 A1 | 12/2009 | Brauer et al. | |
| 2010/0010330 A1 | 1/2010 | Rankers et al. | |
| 2010/0081911 A1 | 4/2010 | Sloan et al. | |
| 2010/0105999 A1 | 4/2010 | Dixon et al. | |
| 2010/0256047 A1 | 10/2010 | Sieh et al. | |
| 2010/0317953 A1 | 12/2010 | Reggiardo et al. | |
| 2010/0331654 A1 | 12/2010 | Jerdonek et al. | |
| 2011/0047499 A1 | 2/2011 | Mandro et al. | |
| 2011/0166544 A1 | 7/2011 | Verhoef et al. | |
| 2011/0178717 A1 | 7/2011 | Goodnow et al. | |
| 2011/0193704 A1 | 8/2011 | Harper et al. | |

* cited by examiner

HANDHELD DIABETES MANAGER WITH A USER INTERFACE FOR DISPLAYING A STATUS OF AN EXTERNAL MEDICAL DEVICE

CROSS-REFERENCE TO RELATED APPLICATIONS

This application claims the benefit of U.S. provisional application No. 61/581,149 filed on Dec. 29, 2011. The disclosure of the above application is incorporated herein by reference in its entirety.

FIELD

The present disclosure relates to a handheld diabetes manager that includes a user interface for a blood glucose meter and an insulin pump.

BACKGROUND

Diabetes mellitus, often referred to as diabetes, is a chronic condition in which a person has elevated blood glucose levels that result from defects in the body's ability to produce and/or use insulin. There are three main types of diabetes. Type 1 diabetes usually strikes children and young adults, and may be autoimmune, genetic, and/or environmental. Type 2 diabetes accounts for 90-95% of diabetes cases and is linked to obesity and physical inactivity. Gestational diabetes is a form of glucose intolerance diagnosed during pregnancy and usually resolves spontaneously after delivery.

Diabetes is managed primarily by controlling the level of glucose in the bloodstream. This level is dynamic and complex, and is affected by multiple factors including the amount and type of food consumed, and the amount of insulin (which mediates transport of glucose across cell membranes) in the blood. Blood glucose levels are also sensitive to exercise, sleep, stress, smoking, travel, illness, menses, and other psychological and lifestyle factors unique to individual patients. The dynamic nature of blood glucose and insulin, and all other factors affecting blood glucose, often require a person with diabetes to forecast blood glucose levels. Therefore, therapy in the form of insulin or oral medications, or both, can be timed to maintain blood glucose levels in an appropriate range.

Management of diabetes is time-consuming for patients because of the need to consistently obtain reliable diagnostic information, follow prescribed therapy, and manage lifestyle on a daily basis. Diagnostic information, such as blood glucose, is typically obtained from a capillary blood sample with a lancing device and is then measured with a handheld blood glucose meter. Interstitial glucose levels may be obtained from a continuous glucose sensor worn on the body. Prescribed therapies may include insulin, oral medications, or both. Insulin can be delivered with a syringe, an ambulatory infusion pump, or a combination of both. With insulin therapy, determining the amount of insulin to be injected can require forecasting meal composition of fat, carbohydrates and proteins along with effects of exercise or other physiologic states. The management of lifestyle factors such as body weight, diet, and exercise can significantly influence the type and effectiveness of a therapy.

Management of diabetes involves large amounts of diagnostic data and prescriptive data acquired in a variety of ways: from medical devices, from personal healthcare devices, from patient-recorded logs, from laboratory tests, and from healthcare professional recommendations. Medical devices include patient-owned bG meters, continuous glucose monitors, ambulatory insulin infusion pumps, diabetes analysis software, and diabetes device configuration software. Each of these systems generates and/or manages large amounts of diagnostic and prescriptive data. Personal healthcare devices include weight scales, blood pressure cuffs, exercise machines, thermometers, and weight management software. Patient recorded logs include information relating to meals, exercise and lifestyle. Lab test results include HbA1C, cholesterol, triglycerides, and glucose tolerance. Healthcare professional recommendations include prescriptions, diets, test plans, and other information relating to the patient's treatment.

Patients using insulin pumps or other external devices can benefit from a diabetes manager with a user interface for blood glucose measurements and for communicating with the external devices as provided in this disclosure.

SUMMARY

This section provides a general summary of the disclosure, and is not a comprehensive disclosure of its full scope or all of its features.

The present teachings provide a handheld diabetes manager that has a graphical user interface for displaying status of an external medical device and includes a port configured to receive a test strip and a blood glucose measurement module. The diabetes manager includes a communications module that selectively communicates via a wireless data link with an external medical device to receive status data pertaining to the operation of the external medical device, and a user interface module in data communication with the blood glucose measurement module and the communications module. The graphical user interface includes a status screen that presents data pertaining to a glucose measure determined by the blood glucose measurement module concurrently with the status data received from the external medical device, such that the status data of the external medical device is presented on the status screen only when the communication module is in data communication with the external medical device.

In some embodiments, the external device is an insulin pump. In some embodiments, more than one external device communicates wirelessly with the diabetes manager. In some embodiments, the graphical user interface includes a status screen that presents data pertaining to a glucose measure determined by the blood glucose measurement module concurrently with the status data received from the external medical device, such that the status data of the external medical device is presented on the status screen only when the communication module is in data communication with the external medical device.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
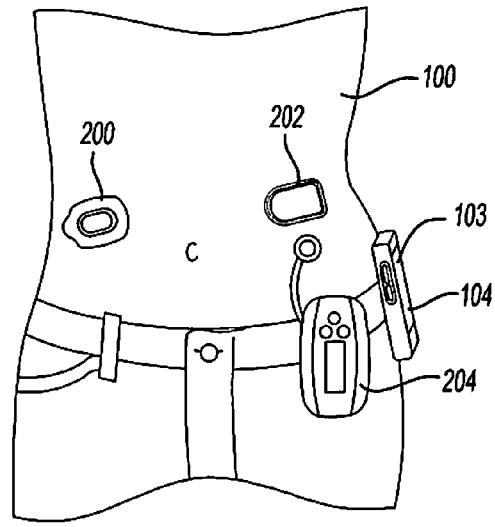
FIG. 1 shows a patient with a continuous glucose monitoring (CGM) patch, an ambulatory durable insulin infusion pump, an ambulatory non-durable insulin infusion pump, and a diabetes manager.

The following description is merely illustrative in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method may be executed in different order without altering the principles of the present disclosure.

Referring now to FIG. 1, a person with diabetes 100 using various medical devices is illustrated. Persons with diabetes include persons with metabolic syndrome, persons with pre-diabetes, type 1 diabetics, type 2 diabetics, and gestational diabetics and are collectively referred to as a patient. Healthcare providers for diabetes are diverse and include nurses, nurse practitioners, physicians, and endocrinologists and are collectively referred to as a clinician.

During a healthcare consultation, the patient 100 typically shares with the clinician a variety of patient data including blood glucose measurements, continuous glucose monitor data, amounts of insulin infused, amounts of food and beverages consumed, exercise schedules, and other lifestyle information. The clinician may obtain additional patient data that includes measurements of HbA1C, cholesterol levels, triglycerides, blood pressure, and weight of the patient 100. The patient data can be recorded manually or electronically on a handheld diabetes management device 104 having a display 103, a diabetes analysis software executed on a personal computer (PC), and/or a web-based diabetes analysis site (not shown). The clinician can analyze the patient data manually or electronically using the diabetes analysis software and/or the web-based diabetes analysis site. After analyzing the patient data and reviewing adherence of the patient 100 to previously prescribed therapy, the clinician can decide whether to modify the therapy for the patient 100.

Referring now to FIG. 1, the patient 100 can use a continuous glucose monitoring (CGM) device or CGM patch 200, an ambulatory non-durable insulin infusion pump 202 or an ambulatory durable insulin infusion pump 204 (hereinafter insulin pump 202 or 204), and the handheld diabetes management device 104 (hereinafter the diabetes manager or meter 104). The CGM patch 200 includes a body mount, a reusable component and a subcutaneous sensor to sense and monitor the amount of glucose in interstitial fluid of the patient 100 and communicates corresponding data to the diabetes manager 104.

The diabetes manager 104 can perform various tasks including measuring and recording blood glucose levels, determining an amount of insulin to be administered to the patient 100 via the insulin pump 202 or 204, receiving patient data via a user interface, archiving the patient data, etc. The diabetes manager 104 periodically receives data from the CGM patch 200 from which glucose levels of the patient 100 are computed. The diabetes manager 104 transmits instructions to the insulin pump 202 or 204, which delivers insulin to the patient 100. Insulin can be delivered in a scheduled manner in the form of a basal dose, which maintains a predetermined insulin dose to the patient 100. Additionally, insulin can be delivered in the form of a bolus dose, which raises the amount of insulin delivered to the patient 100 by a predetermined amount.

Figure 2:
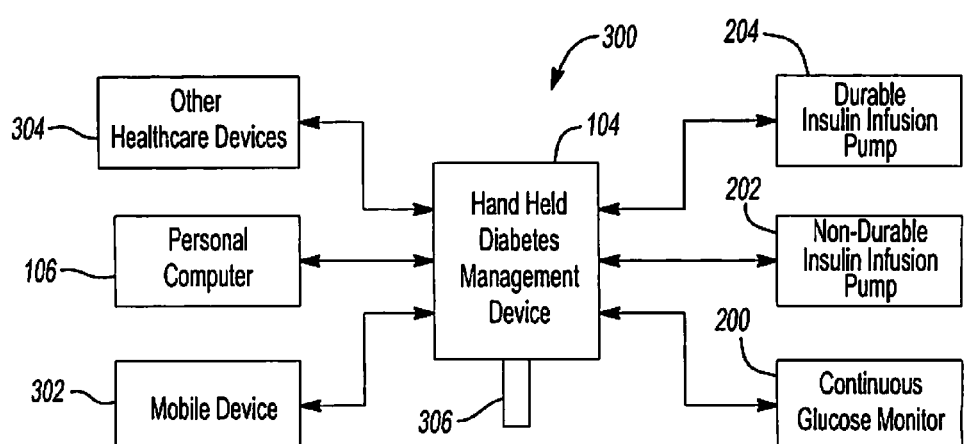
FIG. 2 shows a diabetes management system used by patients and clinicians to manage diabetes.

Generally, and referring now to FIG. 2, a diabetes management system 300 used by the patient 100 and the clinician can include one or more of the following devices: the diabetes manager 104, the continuous glucose monitor (CGM patch) 200, the insulin pump 202 or 204, a mobile device 302, the PC 106 with diabetes analysis software, and other healthcare devices 304. The diabetes manager 104 can be configured as a system hub that communicates with the devices of the diabetes management system 300. Alternatively, the mobile device 302 can serve as the system hub. Communication between the devices in the diabetes management system 300 can be performed using wireless interfaces (e.g., Bluetooth) and/or wireline interfaces (e.g., USB). Communication protocols used by these devices can include protocols compliant with the IEEE 11073 standard, as extended using guidelines provided by Continua® Health Alliance Design Guidelines. Further, healthcare records systems such as Microsoft® HealthVault™ and Google™ Health can be used by the patient 100 and clinician 102 to exchange information.

The diabetes manager 104 can receive glucose readings from one or more sources (e.g., from the CGM patch 200). The CGM patch 200 continuously monitors the glucose level of the patient 100. The CGM patch 200 periodically communicates data to the diabetes manager 104 from which the diabetes manager 104 computes glucose levels of the patient. The diabetes manager 104 and the CGM patch 200 communicate wirelessly using generally a proprietary wireless protocol, such as, for example, the Gazell wireless protocol developed by Nordic Semiconductor, Inc., Sunnyvale, Calif. Any other suitable wireless protocol can be used instead.

Additionally, the diabetes manager 104 includes a blood glucose meter (BGM) and a port that communicates with the BGM (not shown). The port can receive a blood glucose measurement strip 306. The patient 100 deposits a sample of blood on the blood glucose measurement strip 306. The BGM analyzes the sample and measures the blood glucose level in the sample. The blood glucose level measured from the sample and/or the glucose level computed using data received from the CGM patch 200 can be used to determine the amount of insulin to be administered to the patient 100.

The diabetes manager 104 can also communicate with the insulin pump 202 or 204. The insulin pump 202 or 204 can be configured to receive instructions from the diabetes manager 104 to deliver a predetermined amount of insulin to the patient 100. Additionally, the insulin pump 202 or 204 can receive other information including meal and/or exercise schedules of the patient 100. The insulin pump 202 or 204 can determine the amount of insulin to administer based on the additional information.

The insulin pump 202 or 204 can also communicate data to the diabetes manager 104. The data can include amounts of insulin delivered to the patient 100, corresponding times of delivery, and pump status. The diabetes manager 104 and the insulin pump 202 or 204 can communicate using a wireless communication protocol such as Bluetooth. Other wireless or wireline communication protocols can also be used.

In addition, the diabetes manager 104 can communicate with the other healthcare devices 304. For example, the other healthcare devices 304 can include a blood pressure meter, a weight scale, a pedometer, a fingertip pulse oximeter, a thermometer, etc. The other healthcare devices 304 obtain and communicate personal health information of the patient 100 to the diabetes manager 104 through wireless, USB, or other interfaces. The other healthcare devices 304 may use communication protocols compliant with ISO/IEEE 11073 extended using guidelines from Continual® Health Alliance. The diabetes manager 104 can communicate with the other healthcare devices 304 using interfaces including Bluetooth, USB, etc. Further, the devices of the diabetes management system 300 can communicate with each other via the diabetes manager 104.

The diabetes manager 104 can communicate with the PC 106 using Bluetooth, USB, or other interfaces. A diabetes management software running on the PC 106 includes an analyzer-configurator that stores configuration information of the devices of the diabetes management system 300. The configurator has a database to store configuration information of the diabetes manager 104 and the other devices. The configurator can communicate with users through standard web or computer screens in non-web applications. The configurator transmits user-approved configurations to the devices of the diabetes management system 300. The analyzer retrieves data from the diabetes manager 104, stores the data in a database, and outputs analysis results through standard web pages or computer screens in non-web based applications.

The diabetes manager 104 can communicate with the mobile device 302 using Bluetooth. The mobile device 302 may include a cellular phone, a pager, or a personal digital assistant (PDA). The diabetes manager 104 can send messages to an external network through the mobile device 302. The mobile device 302 can transmit messages to the external network upon receiving requests from the diabetes manager 104.

Figure 3:
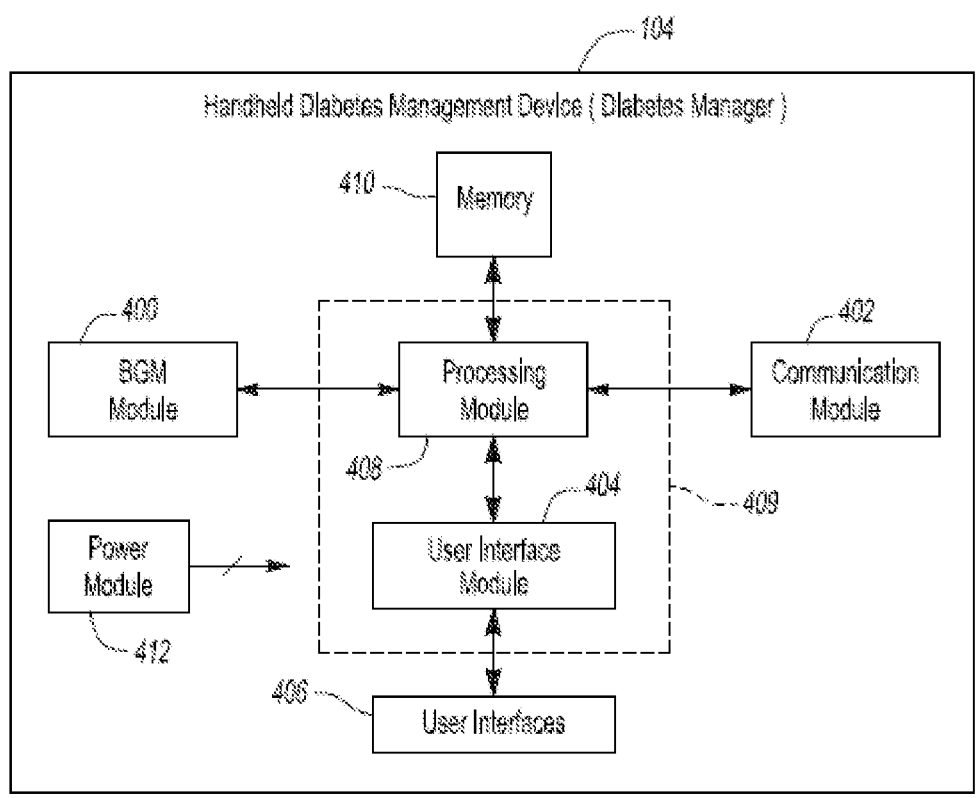
FIG. 3 is a functional block diagram of a diabetes manager according to the present teachings.

Referring now to FIG. 3, the diabetes manager 104 comprises a blood glucose measuring (BGM) module 400, a communication module 402, a user interface module 404, user interfaces 406, a processing module 408, memory 410, and a power module 412. The user interface module 404 and the processing module 408 can be implemented by an application processing module 409. The BGM module 400 includes a blood glucose measuring engine that analyzes samples provided by the patient 100 on the blood glucose measurement strip 306 and that measures the amount of blood glucose in the samples. The communication module 402 includes multiple radios that communicate with different devices of the diabetes management system 300. The user interface module 404 interfaces the diabetes manager 104 to various user interfaces 406 that the patient 100 can use to interact with the diabetes manager 104. For example, the user interfaces 406 can include keys, switches, a display, a speaker, a microphone, a secure digital (SD) card port, a USB port, etc. (not shown).

The processing module 408 processes data received from the BGM module 400, the communication module 402, and the user interface module 404. The processing module 408 uses memory 410 for processing and storing data. The memory 410 can include volatile and nonvolatile memory. The processing module 408 outputs data to and receives data from the user interfaces 406 via the user interface module 404. The processing module 408 outputs data to and receives data from the devices of the diabetes management system 300 via the communication module 402. The power module 412 supplies power to the components of the diabetes manager 104. The power module 412 can include a rechargeable battery. The battery can be recharged using an adapter that plugs into a wall outlet. The battery can also be charged via the USB port of the diabetes manager 104.

Figure 4:
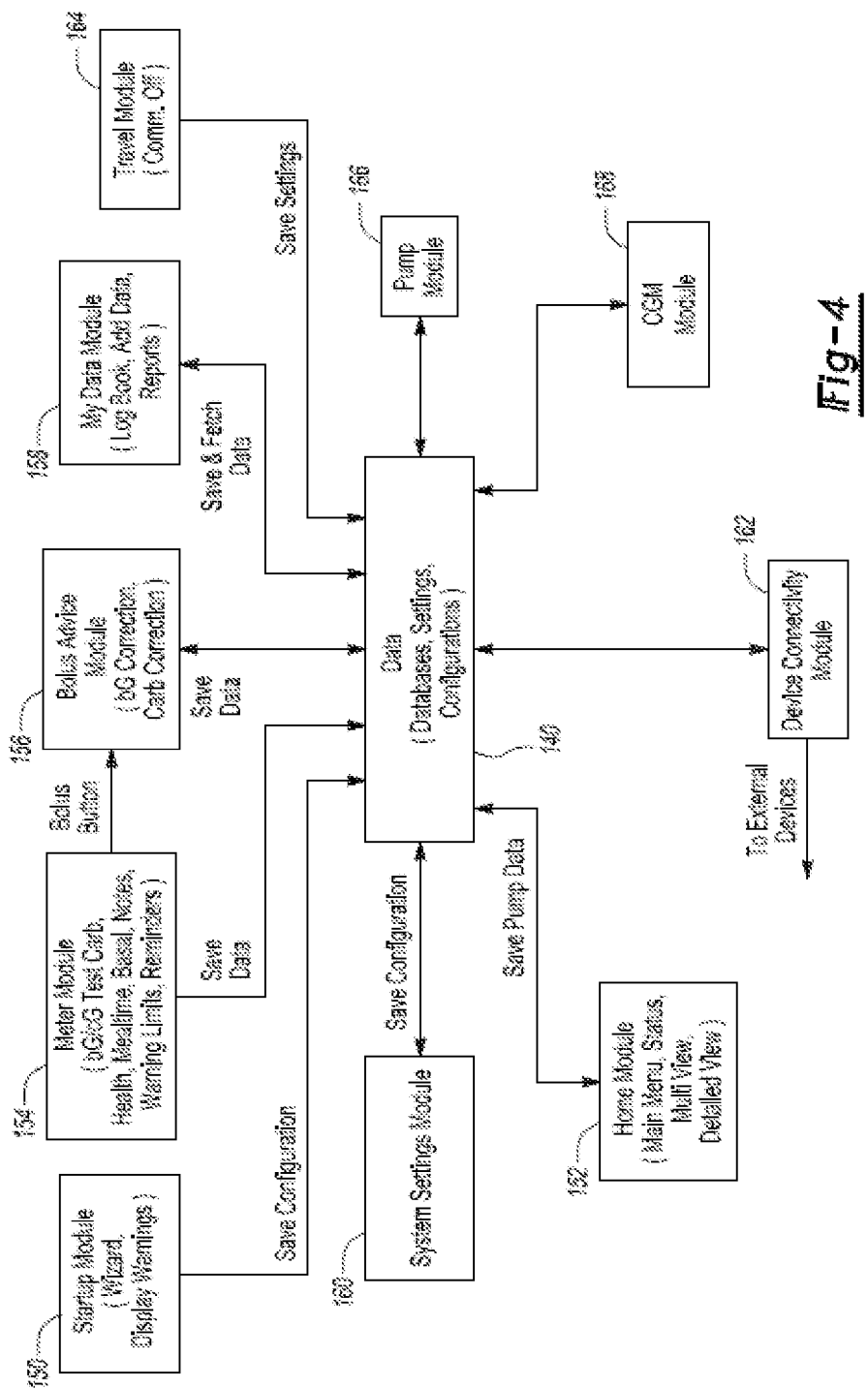
FIG. 4 is a block diagram illustrating a user interface with a home module for a diabetes manager according to the present teachings.

Referring to FIG. 4, a logical screen navigation architecture of the user interface module 404 for handheld diabetes manager 104 is illustrated. The following modules can be integrated in the navigation architecture of the handheld diabetes manager 104: a startup module 150, a home module 152, a meter module 154, a bolus advice module 156, a "my data" module 158, a system settings module 160, a device connectivity module 162, a travel module 164, a pump module 166 and a data module 140. The data module 140 includes databases, settings and configurations, and acts as a central hub that communicates with the other modules to store and provide information related regarding data, settings, configuration related to the other modules. In some embodiments, some of the modules can be removed or inactivated or additional modules can be added. For example, the pump module 166 may be removed or inactivated in models of the handheld diabetes manager 104 for non-pump users. In other modules, a continuous glucose monitoring (CGM) module 168 can be added, as illustrated in dashed lines.

As briefly outlined in reference to FIG. 4, the handheld diabetes manager 104 of the present teachings integrates in a single handheld device various functions, controls, calculations, tests and reports that, in prior art devices, are typically split among different specialized devices, such as single-purpose bG meters, single-purpose remote devices for insulin pumps and other similar single or limited-purpose diabetes managers. Integrating the multiple tasks and functions of the plurality of modules of the handheld diabetes manager 104 of the present teachings requires a user interface that does not simply superpose various functions in an additive manner, but anticipates use case scenarios that are unique and emerge from the interaction of the multiplicity of modules when all these modules are integrated in the same handheld device. Such interactions arise not just from the hardware aspects of the device, but from the various possibilities or use scenarios that a user may subject the device to based on the user-perceived and/or actual capabilities of the device. For example, although portability is common to many prior art diabetes devices, portability and use in restricted or semi-restricted environments requires anticipation of alternative use case or use scenarios to avoid conflicts, without totally disabling the device. In the following, the term pump is used interchangeably for an insulin pump and insulin patch with CGM device, unless differentiation is required.

In the context of the user interface for the handheld diabetes manager 104, a use case is an observable result based upon an action by a user. A use case describes the behavior and navigation along a primary or alternate path including any standard business rules for diabetes management and is graphically represented in an activity or behavior diagram, as shown for example in FIGS. 9, 11, 13 and 14.

The present teachings are directed generally to the home module 152 of the user interface module 404 (or UI 404, for short). Generally, the home module 152 is configured to present a status screen based on currently connected devices. Accordingly, the user is provided with up to date information at a glance based on the status of the devices. For example, the home module 152 provides different status screen depending on whether the handheld diabetes manager 104 is connected to an insulin pump or a CGM device. Such connection is a wireless connection, although wired connections (such as a USB cable link) can also be used. If no such devices are connected, the status screen presents the most recent bG information, such as, for example, carb, health, basal and meal information. If the handheld diabetes manager 104 is connected to an insulin pump (or CGM device), both the bG information and the current status of the insulin pump, including current basal, bolus, insulin level and battery information, are displayed, as discussed below.

Figure 5:
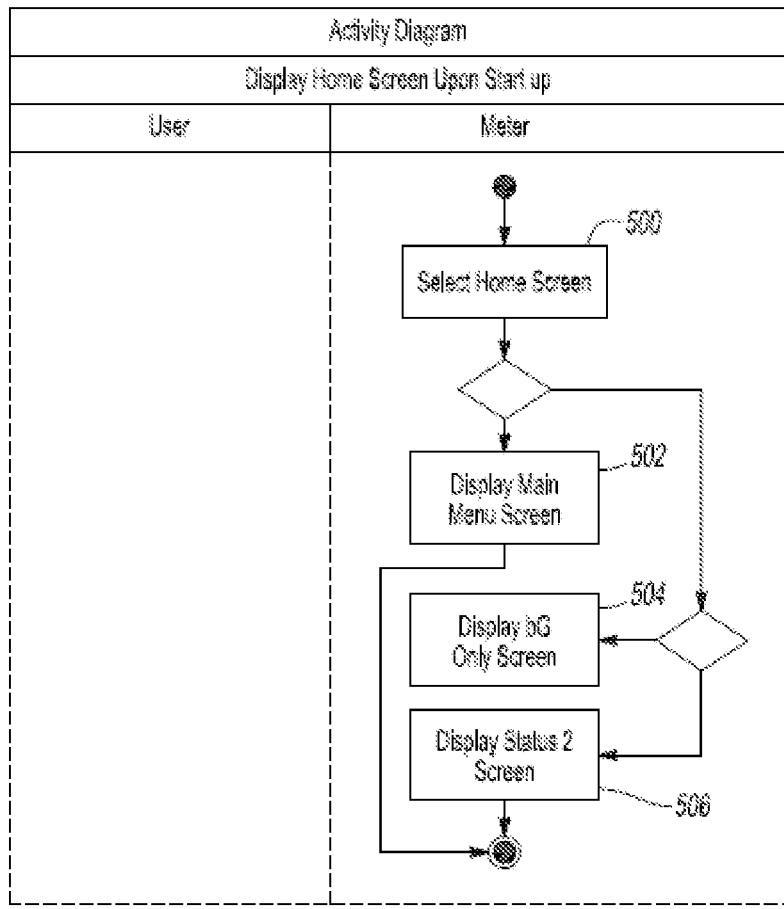
FIG. 5 is an activity diagram illustrating behavioral flow for selecting screens to be displayed on a home screen of a diabetes manager according to the present teachings.
Figure 8:
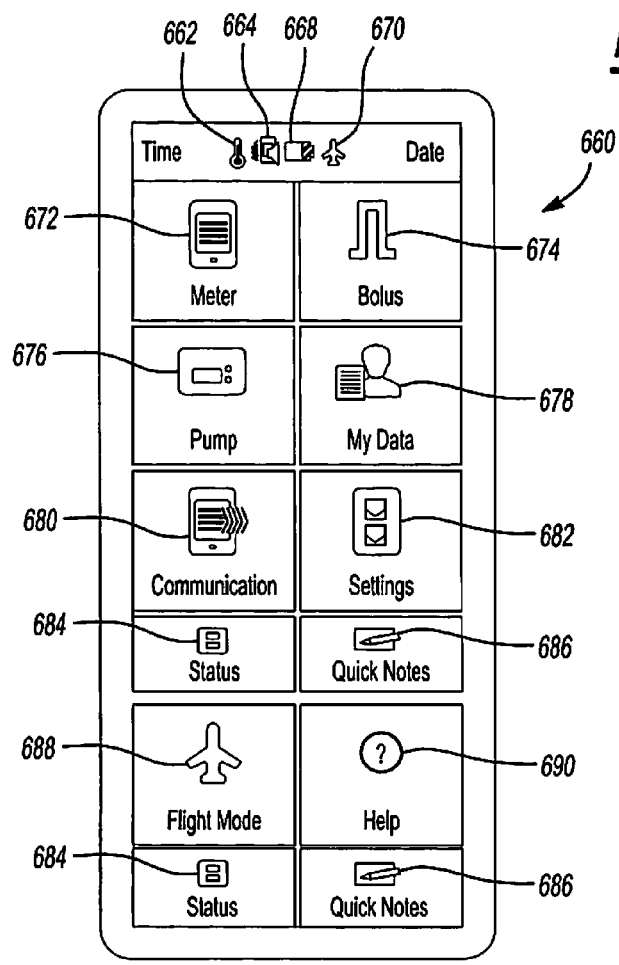
FIG. 8 is an exemplary main menu screen of a diabetes manager according to the present teachings.
Figure 10:
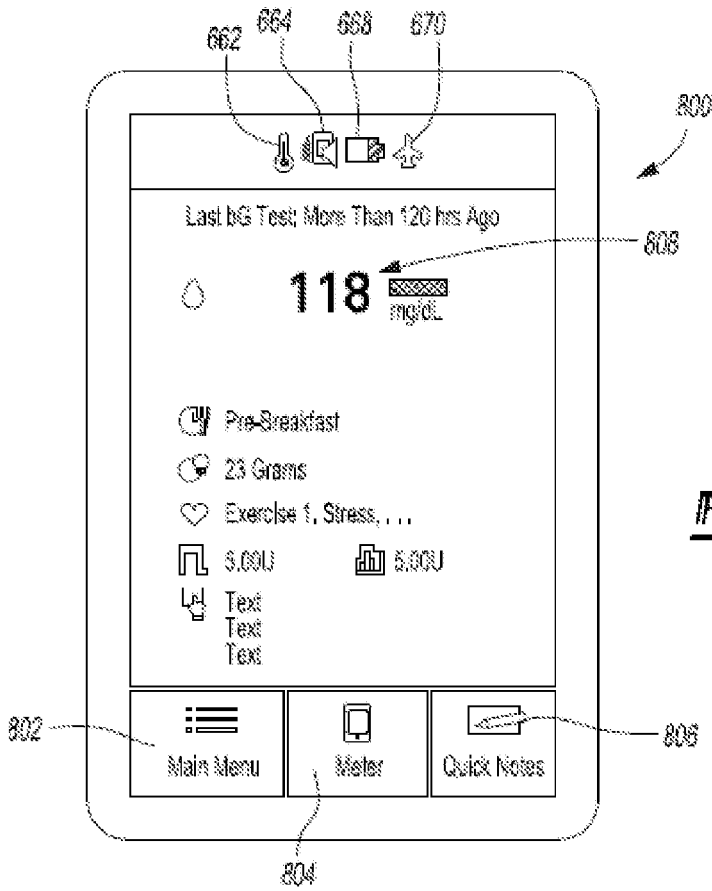
FIG. 10 is an exemplary status screen of a diabetes manager according to the present teachings.
Figure 12:
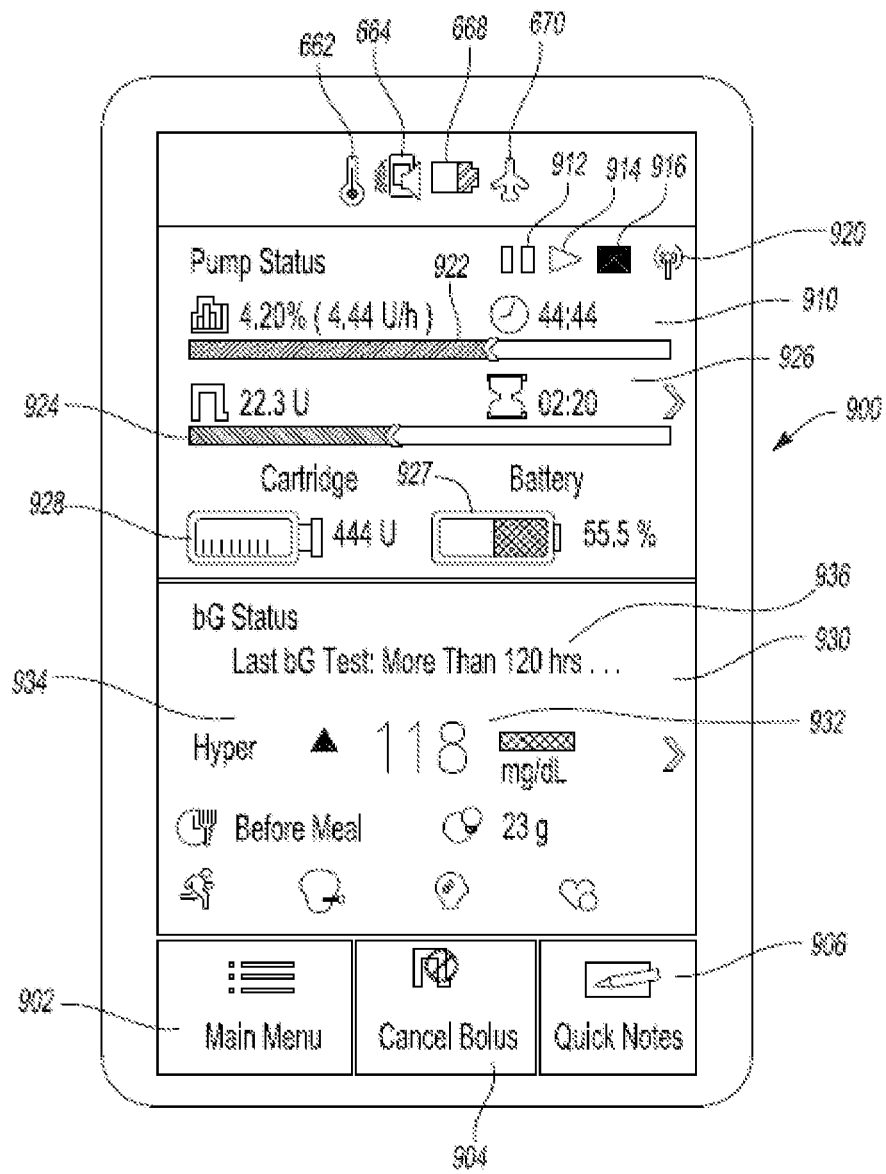
FIG. 12 is another exemplary status screen of a diabetes manager according to the present teachings.

Referring to FIG. 5, an activity diagram implementing the behavior of the user 100 and diabetes manager 104 for the home module 152 (shown in FIG. 4) is illustrated. At block 500, a specific home screen is selected for display at startup. The home screen can be a main menu screen or a status screen. The user can select which home screen is displayed via the system settings module 160 (FIG. 4) by pressing a settings button, such as button 682 (FIG. 8) and making a selection under a meter settings option. When the main menu screen is selected as the home screen, then the main menu screen is displayed (block 502). An exemplary main menu screen is illustrated in FIG. 8 (discussed below). When the status screen is selected as a home screen, then one of two different status screens are displayed as follows. When the handheld diabetes manager 104 is not paired or otherwise connected to another device, such as a pump 202, 204 or a CGM patch 200, then a bG status screen, i.e., a screen displaying only bG information is displayed (block 504). An exemplary bG only status screen is shown in FIG. 10 (discussed below). When the handheld diabetes manager 104 is paired or otherwise connected to another device, such as a pump 202, 204 or a CGM patch 200, then a second status screen (or status 2) is displayed (block 506). An exemplary second status screen is illustrated in FIG. 12 (discussed below).

Figure 6:
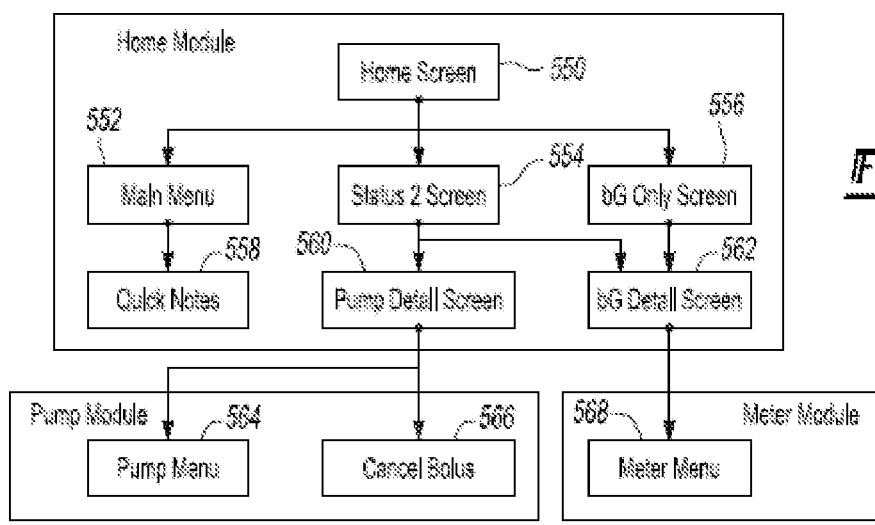
FIG. 6 is a block diagram illustrating a home screen selection of a diabetes manager according to the present teachings.

A use case map of the home module 152 illustrating the above rules is shown in FIG. 6. More specifically, a home screen (block 550) can be set to main menu screen (block 552) or to one of two status screens, i.e., the bG only screen (block 556) or the status 2 screen (block 554). From the main menu screen (block 552), a Quick Notes screen (block 558) can be selected and displayed. The Quick Notes screen (block 558) displays, for example, meal and various lifestyle activities and is discussed below in connection with FIG. 13. From the status 2 screen (block 554), pump detail screen 560 or bG detail screen (block 562) can be selected and displayed. Pump (or other device) detail screen (block 560) displays details of the pump 202, 204 (or other paired devices, such as CGM patch 200). The bG detail screen (block 562) displays details of the bG status. The bG detail screen (block 562) can also be entered from the bG only screen (block 556). From the pump detail screen (block 560), a pump menu screen (block 564) or a cancel bolus screen (block 566) can be selected. From the bG detail screen (block 562), a bG meter menu screen (block 568) can be selected.

Figure 7:
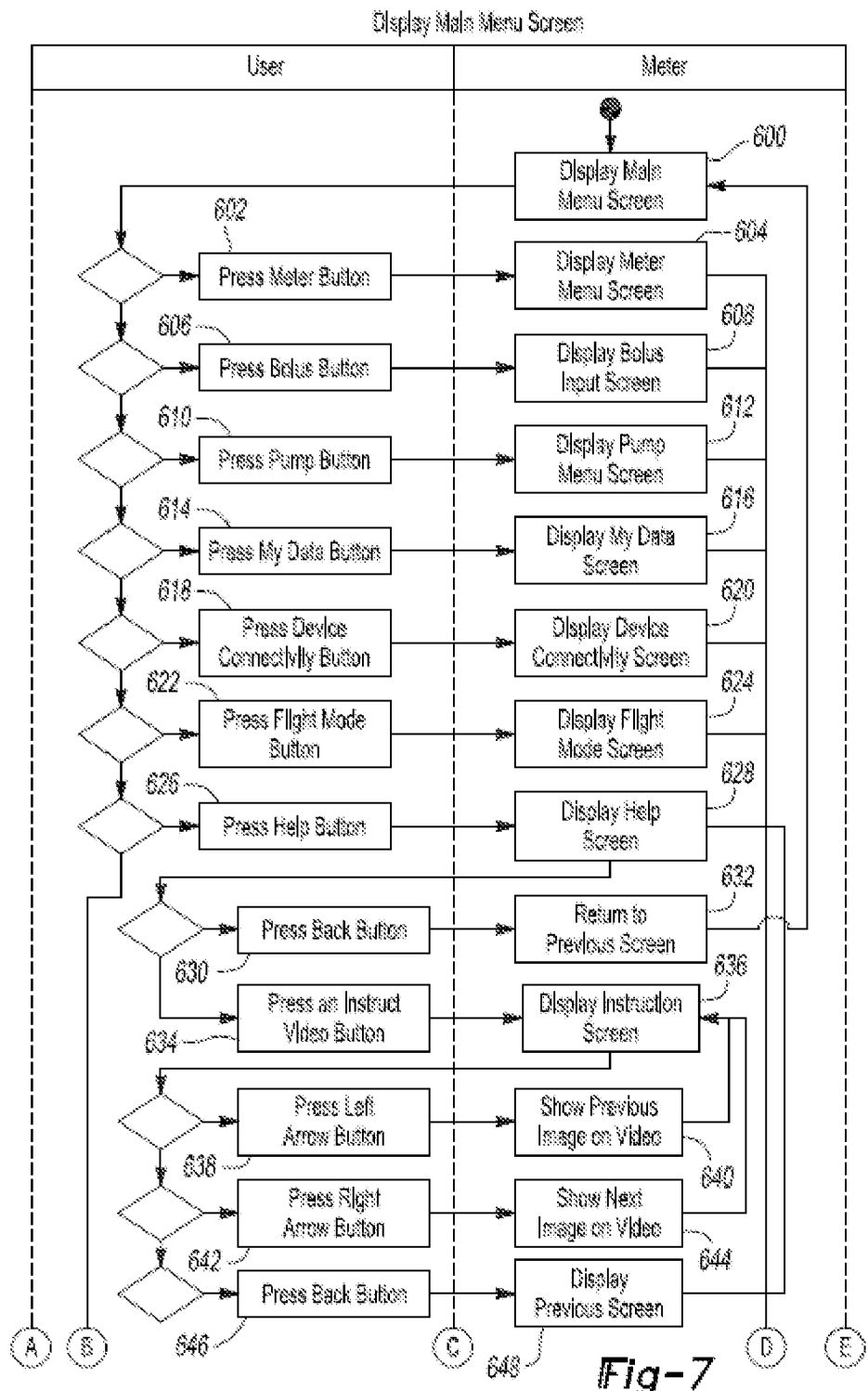
FIG. 7 (shown as FIGS. 7 and 7A) is an activity diagram illustrating behavioral flow for selecting options from a main menu of a diabetes manager according to the present teachings.

Referring to FIGS. 7 and 8, the user interface for the main menu is described. More specifically, a main menu screen 660 can display, as shown in FIG. 8, time and date information, and various status icons, such as, for example a temperature icon 662, sound icon 664 (including vibrate mode), battery status icon 668 and flight mode icon 670. Some status icons are displayed when they are enabled or active. For example, if flight mode is enabled, the flight mode icon 670 is displayed. Similarly, the sound and sound/vibrate icons 664 are displayed when the corresponding functions are enabled. The temperature icon 662 is displayed when the diabetes manager 104 detects that the temperature is outside a bG test warning temperature or a bG test lockout range as defined by a code key for the test strip 306. The battery icon 668 displays the current charge condition of the battery.

The main menu screen 660 includes various buttons (mechanical or touch buttons) that can be activated by touch or stylus or other selector device to display a corresponding detailed screen. The user interface for the main menu screen is generally device-centric, i.e., it is organized and centered about connected or connectable devices according to a predetermined or preselected hierarchy, rather than being centered about functions or capabilities of the handheld diabetes manager 104. The connected or connectable devices in the hierarchy of the user interface can include internal and external devices. An internal device can be, for example, a bG meter or "meter" associated with the user interface meter module 154 (FIG. 4) and the blood glucose measurement (BGM) module 400 (FIG. 3). External devices can include a pump, such as pumps 202, 204, a CGM patch 200 and/or other devices described above in connection with FIG. 2. In FIG. 8, the button labeled meter 672 represents the user interface meter module 154 and interfaces with the internal device for the BGM module 400. The button labeled pump 676 illustrates the user interface for an external device, in this case a pump, as shown in the user interface pump module 156 (FIG. 4) and in FIG. 2 at 202 and 204. Another button corresponding to the user interface for a CGM module 168 (FIG. 4) and at 200 in FIG. 2 can be added, as well as buttons for additional external devices. The pump button 676 is used to represent any such external devices, with the insulin infusion pumps 202, 204 and the CGM patch 200 being exemplary devices.

With continued reference to FIG. 8, the main menu screen 660 can include a bolus button 674 corresponding to the user interface bolus advice module 156, a My Data button 678 corresponding to the user interface my data module 158, a communications button 680 corresponding to the user interface device connectivity (or communications) module 162, and a setting button 682 corresponding to the user interface system setting module 160. The main menu screen 660 can also include a status button 684, and a quick notes button 686. A flight mode button 688 and a help button 690 (indicated as a question mark) can be presented and accessed by swiping the screen. The flight mode button 688 and the help button 690 then cover the immediately preceding set of buttons, such as the communication button 680 and the settings button 682.

Pressing (or touching) any of the buttons in the main menu screen 660 leads to a more detailed screen for the function of the button that was pressed. Referring to FIG. 7, for example, a self-explanatory activity diagram is illustrating using blocks. Starting from the main menu screen (block 600), pressing the meter button (block 602) displays the meter menu screen (block 604); pressing the bolus button (block 606) displays the bolus input screen (block 608); pressing the pump button (block 610) displays the pump menu screen (block 612); pressing the my data button (block 614) displays the my data screen (block 616); pressing device connectivity/communication button (block 618) displays the device connectivity/communication screen (block 620); and pressing the flight mode button (block 622) displays the flight mode screen (block 624). If the diabetes manager 104 is paired with the pump 202, 204, the pump button 676 is displayed. If the diabetes manager 104 is not paired with the pump 202, 204, then the pump button 676 is disabled. The communication button 680 and the flight mode button 688 may be shifted up by a swiping gesture of the user. If the diabetes manager 104 is paired with the pump 202, 204 and the flight mode is enabled, then the pump button 676 will be disabled. When the diabetes manager is in communication with the pump 202, 204, a communication icon 680 can be displayed on the pump button 676. The bolus button 674 can disable a bolus advice icon if bolus advice is enabled, or just a bolus icon if bolus advice is not enabled.

Additionally, pressing the help button 690 (block 626) displays the help screen (block 628). From the help screen (block 628), the user can press a back button (block 630) and return to the previous screen (block 632), such as the main menu screen (block 600). Alternatively, from the help screen (block 628), the user can press an "instruct video" button (block 634) to display an instruction screen (block 636) with an associated instructional video. If there are no videos available, the instruction screen displays a message to that effect. From the instruction screen pressing a left arrow button (block 638), will display the previous image on video (block 640), pressing a right arrow button (block 642) will display the next image on video (block 644). Pressing a back button (block 646) will display the previous screen (block 648), such as the main menu screen (block 600).

Figure 7A:
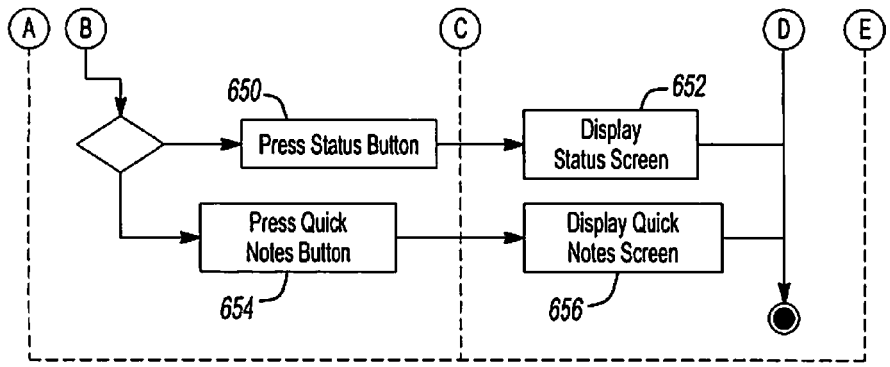

With continued reference to FIG. 7, FIGS. 7A and 8, pressing the status button 684 (block 650) displays the status screen (block 652) and pressing the quick notes button 686 (block 654) displays the quick notes screen (block 656).

Figure 9:
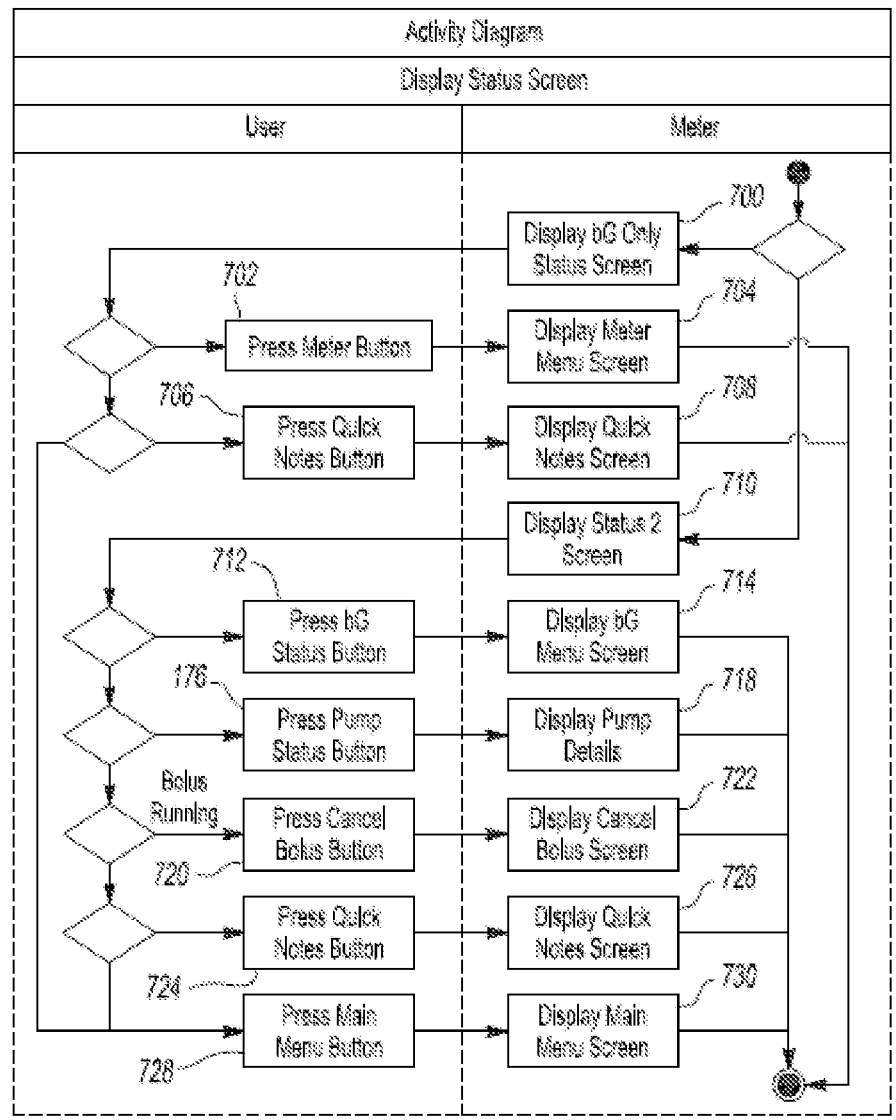
FIG. 9 is an activity diagram illustrating behavioral flow for displaying a status screen of a diabetes manager according to the present teachings.
Figure 11:
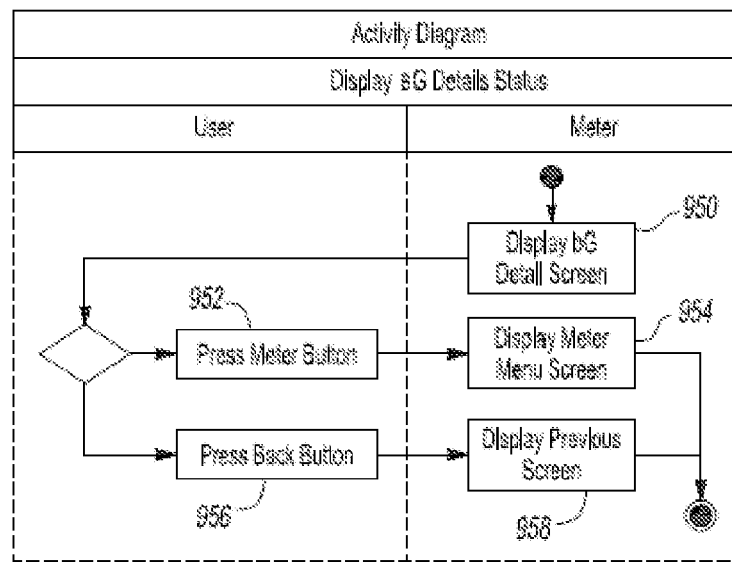
FIG. 11 is an activity diagram illustrating business rules for displaying a bG details status screen of a diabetes manager according to the present teachings.

Referring to FIG. 9-12, an activity diagram of the business rules associated with displaying the status screen is illustrated in FIG. 9, a bG only status screen is shown in FIG. 10, an activity diagram for displaying the detailed bG status is shown in FIG. 11 and a bG and pump status screen (status 2 screen) is shown in FIG. 12. As discussed above in relation to FIGS. 5 and 6, when the handheld diabetes manager 104 is not paired or otherwise connected to another device, such as a pump 202, 204 or a CGM patch 200, then a bG status screen 800, i.e., a screen displaying only bG information is displayed, as shown in FIG. 10. When the handheld diabetes manager 104 is paired or otherwise connected to another device, such as a pump 202, 204 or a CGM patch 200, then a second status screen (or status 2) 900 is displayed including bG status and pump (or other device) status, as shown in FIG. 12. More specifically, the option to display the bG only screen 800 is represented at block 700 and the option to display the status 2 screen is represented at block 708. The bG only status screen 800 can include a main menu button 802, a meter button 804 and a quick notes button 806. The diabetes manager 104 is configured such that the bG only status screen 800 will display the bG value and units in the bG field with a bG icon and an appropriate bG range indicator, when the bG value is within the lower and upper limits or thresholds established by the code key, as shown in FIG. 10 at 808. If the bG value is outside the lower or upper limit, the bG field shall display text indicating low or high result accordingly. When the bG value is within the limits of the code key but outside the hyper or hypo warning limits, the bG field shall display text to indicate a hyper or a hypo condition, and related symbols and range indicators accordingly.

When the option to display the bG only screen 800 is activated because the second device or pump 202, 204 or is not connected, pressing the meter button 804 (block 702) displays a meter menu screen (block 704) that includes, for example, a bG test button, warning limits (hypoglycemia and hyperglycemia) and meter reminders. Pressing the quick notes button 806 (block 706) displays the quick notes screen (block 708). The activities related to quick notes are described below in reference to FIGS. 13 and 13A.

With continued reference to FIGS. 9-12, the option to display the status 2 screen 900 is available when a second device is connected with the diabetes manager 104 and is shown in block 710. The status 2 screen 900 can include a main menu button 902, a cancel bolus button 904 and a quick notes button 906. The status 2 screen 900 has an area dedicated to the pump status 910 and an area dedicated to the bG status area 930. The pump status area 910 can include icons indicating the pump status and representing pause 912, run 914, stop 916 and active communication icon 920. The pump status area 910 displays a real-time basal progress bar 922, a basal icon, basal rate value, units, and basal profile name when the pump is delivering basal insulin. The basal progress bar 922 indicates the real-time progress of delivering basal insulin. When pump is delivering a bolus, the pump status area 910 displays a real-time bolus progress bar 924 and bolus icon, bolus value and units. The bolus progress bar 924 indicates the real-time progress of delivering bolus insulin. The bolus icon can change to indicate whether the bolus is standard or extended or a multiwave bolus. If there is a lagtime associated with a standard bolus being delivered, a lagtime icon and lagtime time can be displayed at 926. The pump status area 910 can also include the battery charge level 927 and insulin cartridge level 928.

With continued reference to FIGS. 8-12, in the bG status area 930, the most recent bG test value is displayed with information regarding the time the bG record/test was completed as "x minutes ago" if the test was completed less than two hours ago, or "more than two hours ago" if the bG record was completed between two and 24 hours ago, or "more than x hours" if the bG record was completed more than 24 hours ago (see FIG. 12 at 936). When the bG value is within the lower and upper limits or thresholds established by the code key, the bG status area 930 will display the bG value and units in the bG field with a bG icon and an appropriate bG range indicator, as shown in FIG. 12 at 932. If the bG value is outside the lower or upper limit, the bG field shall display text indicating low or high result accordingly. When the bG value is within the limits of the code key but outside the hyper or hypo warning limits, the bG field shall display text to indicate a hyper or a hypo condition, and related symbols and range indicators accordingly, as shown at 934 in FIG. 12.

With continued reference to FIG. 12, if the pump 202, 204 is not delivering a bolus, the cancel bolus button 904 is disabled and grayed out. When the cancel button 904 is pressed and there is more than one bolus in the pump queue, a cancel bolus screen is displayed. If there is only one bolus of type x, such as standard, extended, multiwave, in the pump queue, a screen requesting confirmation to cancel the particular type x bolus is displayed. If the pump is delivering a bolus or multiple boluses, the bolus information bar's highest priority running bolus is displayed at the top.

Referring to FIGS. 10 and 11, pressing the meter button 804 displays a bG detail screen (block 950). From the bG detail screen, pressing a meter button (block 952) displays a meter menu screen (block 954) and pressing a back button (block 956) displays the previous screen (block 958).

Figure 13:
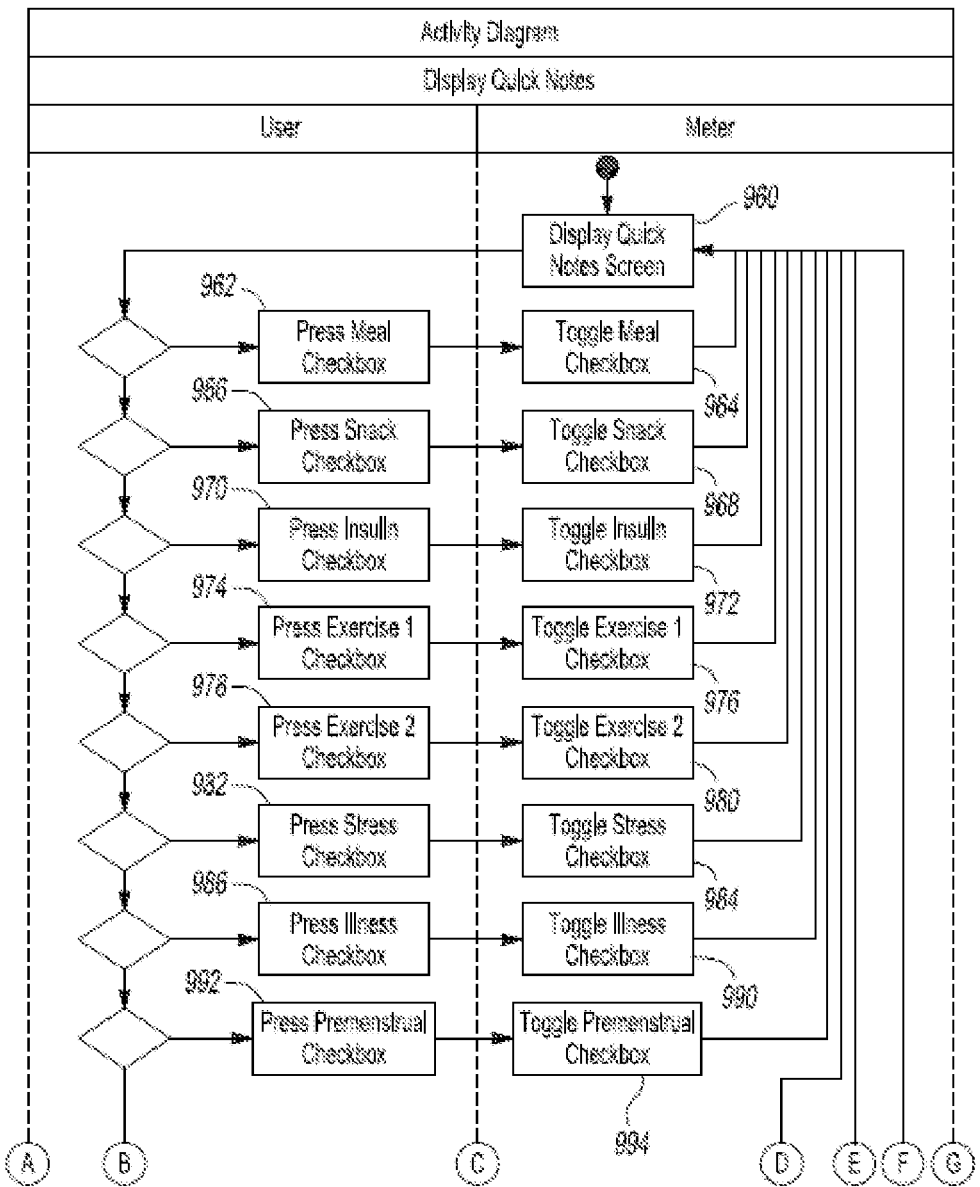
FIG. 13 (shown as FIGS. 13 and 13A) is an activity diagram illustrating behavioral flow for displaying a quick notes screen of a diabetes manager according to the present teachings.
Figure 13A:
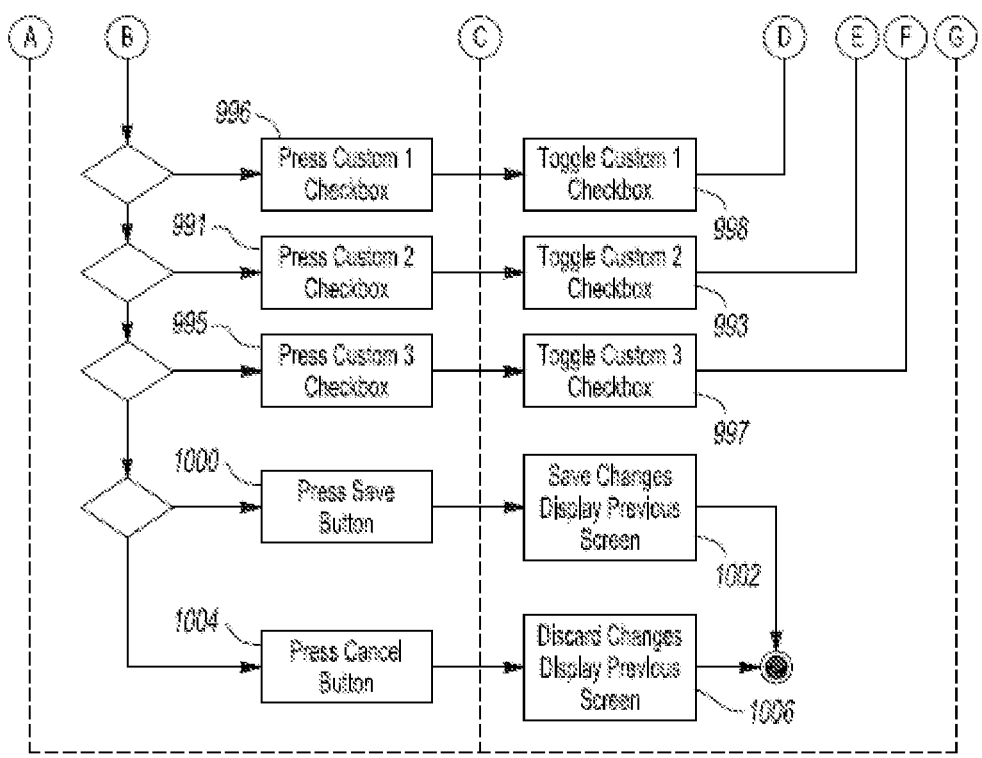

Referring to FIGS. 10 and 13 (shown as FIGS. 13 and 13A), pressing the quick notes button 906 displays the quick notes screen (block 960). The quick notes include information about meals, snacks, insulin, exercise, stress, illness, premenstrual conditions, and other lifestyle and health conditions. The activity diagram of FIG. 13 illustrates various checkboxes that can be pressed by the user leading to a toggle action, i.e., the particular checkbox is checked and unchecked or set to on or off to show that the corresponding activity has taken place. For example, pressing a meal checkbox (block 962) toggles the meal checkbox (block 964) from an off to an on status or from the on status to an off status. Similarly, pressing a snack checkbox (block 966) toggles the snack checkbox (block 968). Pressing an insulin checkbox (block 970) toggles the insulin checkbox (block 972).) (block 972). Pressing an exercise 1 checkbox (block 974) toggles the exercise 1 checkbox (block 976). Pressing an exercise 2 checkbox (block 978) toggles the exercise 2 checkbox (block 980). Pressing a stress checkbox (block 982) toggles the stress checkbox (block 984). Pressing an illness checkbox (block 986) toggles the illness checkbox (block 990). Pressing a premenstrual checkbox (block 992) toggles the premenstrual checkbox (block 994). Accordingly, diet, exercise, health, lifestyle and related events can be saved and viewed using the quick notes screen. Additionally, other such events can be customized. Three such custom checkbox (blocks 996, 991, 995) can be utilized and toggled (blocks 998, 993, 997) for their corresponding information. If one or more checkbox have been toggled, a save button is enabled. Pressing the save button (block 1000), saves the changes and the previous screen is displayed (block 1002). The quick notes data are saved in a logbook that can be accessed via the my data button 678 of the main menu screen 660. In addition to the quick notes saved by toggling, an option to add text notes is presented in a screen showing the quick notes in the logbook. If a cancel button is pressed instead (block 1004), then the changes are discarded and the previous screen is displayed (block 1006).

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories. A maximum number of quick notes checkbox can be set and a warning provided when the maximum number is exceeded.

The apparatuses and methods described herein may be implemented by one or more computer programs executed by one or more processors. The computer programs include processor-executable instructions that are stored on a non-transitory tangible computer-readable medium. The computer programs may also include stored data. Non-limiting examples of the non-transitory tangible computer readable medium are nonvolatile memory, magnetic storage, and optical storage.

The broad teachings of the disclosure can be implemented in a variety of forms. Therefore, while this disclosure includes particular examples, the scope of the disclosure should not be so limited since other modifications will become apparent to the skilled practitioner upon a study of the drawings, the specification, and the following claims.

What is claimed is:

1. A diabetes management system having a handheld diabetes manager communicating with an external medical device configured to perform bolus operations, which is separate from the handheld diabetes manager, the handheld diabetes manager comprising:

a port configured to receive a test strip, wherein the test strip receives a blood sample from a user;

a blood glucose measurement module cooperatively operable with the test strip inserted in the port and determining a glucose measurement based on the blood sample disposed on the test strip;

a communications module selectively communicating with the external medical device via a wireless data link, wherein the communications module receives status data from the external medical device, the status data pertains to the operation of the external medical device;

a display; and a user interface module programmed to display a graphical user interface on the display, the user interface module programmed to exchange data with the blood glucose measurement module and the communications module, wherein the user interface module is programmed to display and receive inputs from the user via the graphical user interface, the graphical user interface includes a status screen, and a first cancel bolus screen, a second cancel bolus screen, wherein the status screen presents data pertaining to the glucose measurement determined by the blood glucose measurement module concurrently with the status data received from the external medical device, the user interface module controls the status screen such that the status data of the external medical device is presented on the status screen only when the communication module is in data communication with the external medical device; and the status screen includes a cancel bolus button that is operable by the user to cancel one or more bolus operation to be performed by the external medical device;

the user interface module, in response to the cancel bolus button being pressed, is programmed to determine a number of bolus operations to be performed by the external medical device from the status data and displays one of the first cancel bolus screen and the second cancel bolus screen, the user interface module is further programmed to presents the first cancel bolus screen in response to a determination that one bolus operation is to be performed, and presents the second cancel bolus screen in response to a determination that more than one bolus operation is to be performed; and the first cancel bolus screen requests confirmation to cancel the one bolus operation and the second bolus screen presents the more than one bolus operation with a highest priority running bolus operation from among the more than one bolus operations displayed at, wherein the user interface model is implemented by computer readable instructions executed by a processor residing on the handheld diabetes manager.

2. The diabetes management system of claim 1, wherein the status screen displays a blood glucose result from a most recent blood glucose test and time information regarding when the blood glucose test was completed.

3. The diabetes management system of claim 2, wherein the status screen displays a warning when a lower or upper threshold of the most recent blood glucose test is exceeded.

4. The diabetes management system of claim 1 further includes an external medical device and the external medical device is an insulin pump.

5. The diabetes management system of claim 4, wherein when the insulin pump is paired with the diabetes manager and the insulin pump is running, the status screen displays a pump running icon.

6. The diabetes management system of claim 4, wherein when the insulin pump is paired with the diabetes manager and the insulin pump is stopped, the status screen displays a pump stop icon.

7. The diabetes management system of claim 4, wherein when the insulin pump is paired with the diabetes manager and the insulin pump is paused, the status screen displays a pump pause icon.

8. The diabetes management system of claim 4, wherein when the insulin pump is paired and communicating with the diabetes manager and the insulin pump is delivering basal insulin, the status screen displays a basal information bar with a basal icon, basal profile, basal rate value and units.

* * * * *